(12) United States Patent
Dyson

(10) Patent No.: US 11,015,199 B2
(45) Date of Patent: May 25, 2021

(54) CANCER THERAPY

(71) Applicant: Swansea University, Swansea (GB)

(72) Inventor: Paul Dyson, Swansea (GB)

(73) Assignee: Swansea University, Swansea (GB)

( * ) Notice: Subject to any disclaimer, the term of this patent is extended or adjusted under 35 U.S.C. 154(b) by 304 days.

(21) Appl. No.: 15/774,569

(22) PCT Filed: Nov. 2, 2016

(86) PCT No.: PCT/GB2016/053386
§ 371 (c)(1),
(2) Date: May 8, 2018

(87) PCT Pub. No.: WO2017/081442
PCT Pub. Date: May 18, 2017

(65) Prior Publication Data
US 2019/0112607 A1 Apr. 18, 2019

(30) Foreign Application Priority Data
Nov. 9, 2015 (GB) ..................... 1519734

(51) Int. Cl.
| C12N 15/113 | (2010.01) |
| C12N 15/88 | (2006.01) |
| A61P 35/00 | (2006.01) |
| A61K 35/74 | (2015.01) |
| A61K 35/00 | (2006.01) |

(52) U.S. Cl.
CPC .......... *C12N 15/1135* (2013.01); *A61K 35/74* (2013.01); *A61P 35/00* (2018.01); *C12N 15/1136* (2013.01); *C12N 15/1137* (2013.01); *C12N 15/88* (2013.01); *A61K 2035/11* (2013.01); *C12N 2310/14* (2013.01); *C12N 2320/32* (2013.01); *C12N 2330/51* (2013.01)

(58) Field of Classification Search
CPC ................................................. C12N 15/1135
See application file for complete search history.

(56) References Cited

U.S. PATENT DOCUMENTS

2010/0189691 A1* 7/2010 Fruehauf ............... C12N 15/111
424/93.2
2011/0280836 A1* 11/2011 Guo ........................ A61P 31/04
424/93.2

FOREIGN PATENT DOCUMENTS

| WO | WO 2004/063331 A2 | 7/2004 |
| WO | WO 2006/032041 A2 | 3/2006 |
| WO | WO 2006/066048 A2 | 6/2006 |
| WO | WO 2008/091375 A2 | 7/2008 |
| WO | WO2009/062199 * | 5/2009 ............... C12Q 1/68 |
| WO | WO 2009/062199 A1 | 5/2009 |
| WO | WO 2010/057009 A1 | 5/2010 |
| WO | WO 2013/117910 A1 | 8/2013 |
| WO | WO 2014/043311 A1 | 3/2014 |
| WO | WO 2015/002969 A1 | 1/2015 |

OTHER PUBLICATIONS

Husseiny et al. (Microbiological Research 163 (2008) 605-615) (Year: 2008).*
Zhongming Jiang et al. ("Using attenuated *Salmonella typhi* as tumor targeting vector for MDR1 siRNA delivery: An experimental study," Cancer Biology & Therapy, 2007; 6:4, 555-560, DOI: 10.4161/cbt.6.4.3850) (Year: 2007).*
Song Aichin (PhD Dissertation. 2011. Shan Dong University "Study on the effect of siRNA targeting on c-myc gene expression on proliferation and apoptosis of Jiyoye cells"). (Year: 2011).*
Accession No. BBE40967, May 22, 2014.
Ahmed et al., "Delivery of siRNAs to cancer cells via bacteria," in *RNA Interference: Challenges and Therapeutic Opportunities*, Sioud, Mouldy (Ed.), pp. 117-129, Humana Press, New York, NY, 2015.
Deng et al., "Enhancement of ovarian cancer chemotherapy by delivery of multidrug-resistance gene small interfering RNA using tumor targeting *Salmonella*," *J Obstet Gynaecol Res.* 41:615-622, 2015.
Guo et al., "Targeting tumor gene by shRNA-expressing *Salmonella*-mediated RNAi," *Gene Ther.* 18:95-105, 2011.
Li et al., "Recombinant attenuated *Salmonella typhimurium* carrying a plasmid co-expressing ENDO-VEGI151 and survivin siRNA inhibits the growth of breast cancer in vivo," *Mol Med Rep.* 7:1215-1222, 2013.
Morrissey et al., "Tumour Targeting with Systemically Administered Bacteria," *Curr Gene Ther.* 10:3-14, 2010.
Shi et al., "Combined prokaryotic-eukaryotic delivery and expression of therapeutic factors through a primed autocatalytic positive-feedback loop," *J Control. Release* 222:130-140, 2016.
Whitten, et al., "Symbiont-mediated RNA interference in insects," *Proc R Soc. B* 283:20160042, 2016.
GB 1519734.6 Search Report dated Aug. 17, 2016 (4 pages).
PCT/GB2016/053386 Search Report and Written Opinion dated Jan. 30, 2017 (15 pages).

* cited by examiner

*Primary Examiner* — Scott Long
(74) *Attorney, Agent, or Firm* — Klarquist Sparkman, LLP

(57) ABSTRACT

The invention relates to a genetically transformed or transfected bacterial cell chromosome wherein said cell is made to express interfering RNA (siRNA) active against at least one gene encoding a cancer promoting or sustaining protein such as an oncogene, a chemo-resistant gene or a metabolic gene; siRNA cassette encoding at least one siRNA active against said gene; a bacterial cell with said siRNA cassette integrated within the bacterial chromosome; a method of treating cancer, particularly but not exclusively prostate, breast or colorectal cancer, employing the use of said bacterial cell with a chromosomally integrated siRNA cassette; and use of said bacterial cell with a chromosomally integrated siRNA cassette to treat said cancer.

13 Claims, 9 Drawing Sheets

Figure 1A:
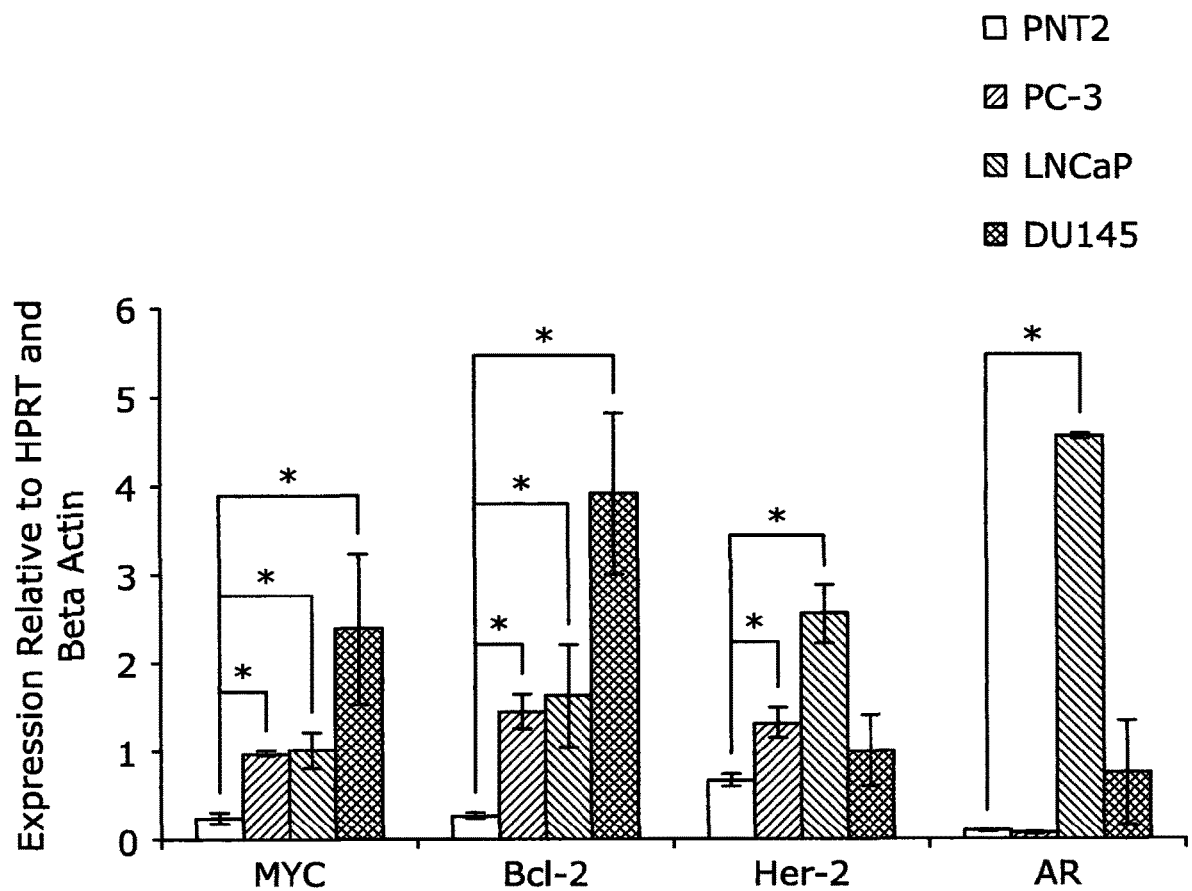

Specification includes a Sequence Listing.

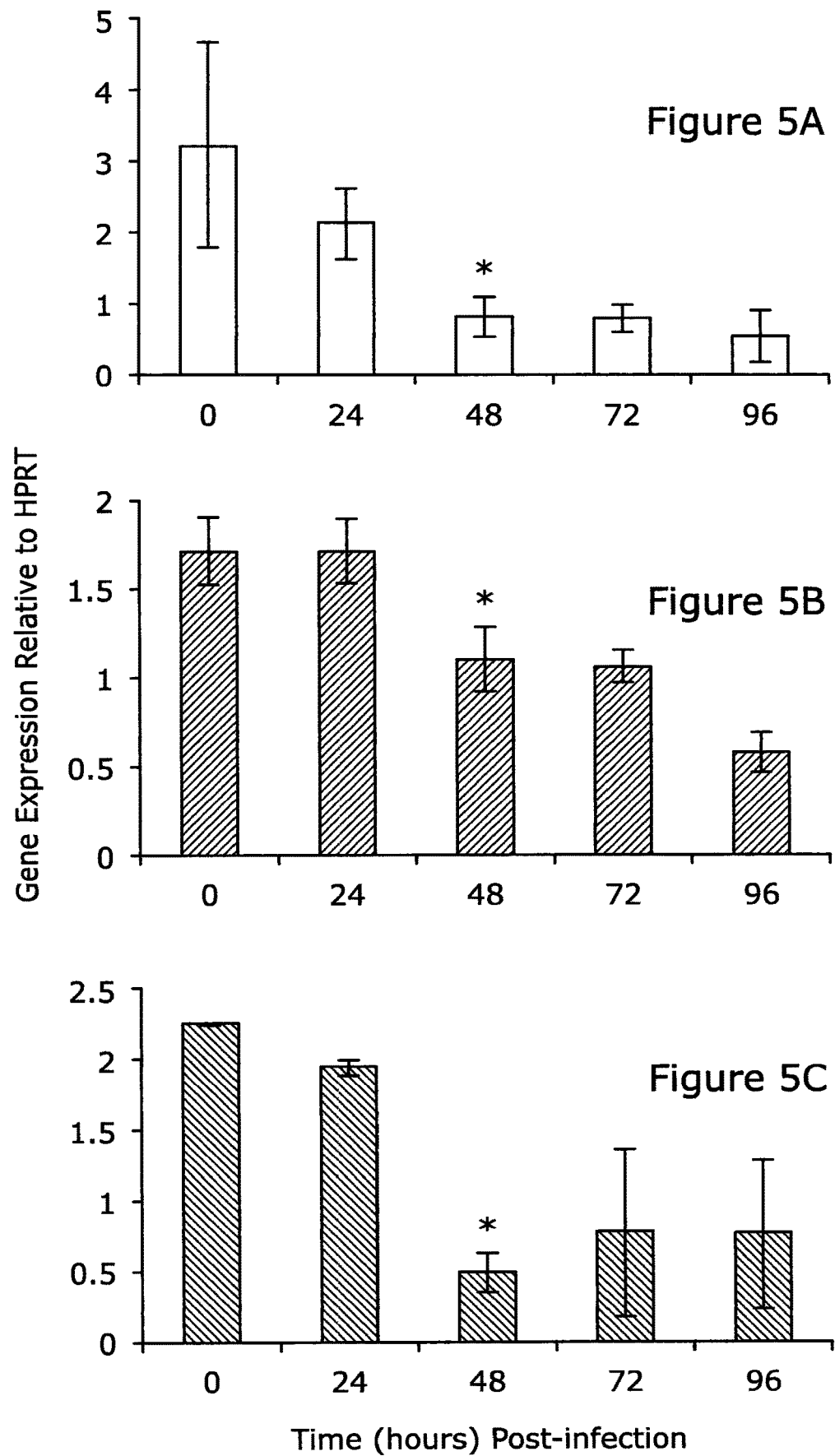

Strategy for chromosomal integration of siRNA cassette exemplified by integration at the *rnc* locus ( ⌐ = restriction site)

CANCER THERAPY

CROSS REFERENCE TO RELATED APPLICATIONS

This is the U.S. National Stage of International Application No. PCT/GB2016/053386, filed Nov. 2, 2016, which was published in English under PCT Article 21(2), which in turn claims the benefit of GB 1519734.6, filed Nov. 9, 2015.

FIELD OF THE INVENTION

The invention relates to a genetically transformed or transfected bacterial cell chromosome wherein said cell is made to express interfering RNA (siRNA) active against at least one gene encoding a cancer promoting or sustaining protein such as an oncogene, a chemo-resistant gene or a metabolic gene; siRNA cassette encoding at least one siRNA active against said gene; a bacterial cell with said siRNA cassette integrated within the bacterial chromosome; a method of treating cancer, particularly but not exclusively prostate, breast or colorectal cancer cancer, employing the use of said bacterial cell with a chromosomally integrated siRNA cassette; and use of said bacterial cell with a chromosomally integrated siRNA cassette to treat said cancer.

BACKGROUND OF THE INVENTION

Since 2012, prostate cancer has become the second most frequently diagnosed cancer (at 15% of all male cancers) and the sixth leading cause of cancer death in males worldwide. In 2010 it resulted in 256,000 deaths, up from 156,000 deaths in 1990. Rates of prostate cancer vary widely across the world. It is least common in South and East Asia, and more common in Europe and North America. In Europe in 2012 it was the 3rd most diagnosed cancer after breast and colorectal at 417,000 cases.

Prostate cancer develops primarily in men over fifty. More than 80% of men will develop prostate cancer by the age of 80. However, in the majority of cases, it will be slow-growing and harmless; however, some prostate cancers grow relatively quickly.

The cancer cells may spread from the prostate to other parts of the body, particularly the bones and lymph nodes. It may initially cause no symptoms. In later stages it can lead to difficulty urinating, produce blood in the urine, and pain in the pelvis or back when urinating. Other late symptoms may include feeling tired due to low levels of red blood cells.

Factors that increase the risk of prostate cancer include: older age, a family history of the disease, and race. Having a first degree relative with the disease increases the risk 2 to 3 fold. In the United States it is more common in the African American population than the Caucasian population.

RNAi is a form of post-transcriptional gene silencing wherein a specific mRNA of a particular gene is destroyed or blocked, preventing translation and formation of an active gene product. RNAi occurs naturally within living cells to modulate gene activity, and is also important in defence against parasites and viral infection.

When a cell is injected with RNA in a double-stranded (ds) form, a protein called Dicer (or RNase III) cleaves the dsRNA molecules into short fragments of RNA (20-25 nucleotides), termed short interfering RNA (siRNA) due to their ability to interfere with the expression of a specific gene. These siRNA molecules are unwound into single stranded (ss) RNA, whereupon the so-called guide strand is incorporated into the RNA-induced silencing complex (RISC). Often, this guide strand will base pair with a complimentary sequence of mRNA in the cell inducing its cleavage by the catalytic component of the RISC complex. The mRNA is not translated and no functional protein is produced, and therefore the effects of the gene encoding the specific mRNA are 'silenced'. This process is termed cell-autonomous RNAi, wherein gene silencing is limited to the cell in which the dsRNA is introduced.

Alternatively, environmental and systemic RNAi are the two forms of non-cell autonomous RNAi, wherein the interfering effect takes place in cells/tissues different from where the dsRNA was introduced/produced. In this case, the dsRNA is either taken up into multiple cells (environmental RNAi such as in viral infections), or the silencing signal is transported from the cell in which the dsRNA is applied or expressed in other cells where the effect is observed (systemic RNAi).

By artificially synthesising dsRNA (or siRNA molecules) with a known sequence complimentary to a gene of interest, and introducing it to target cells, it is possible to understand the role of a specific gene by observing the consequences of its loss of activity. RNAi and other so-called reverse genetics techniques are thus revolutionizing biological sciences, with applications in genomics, biotechnology, and medicine.

We describe herein a new RNAi delivery technique which delivers siRNA molecules effective against transformed cells which express cancer genes.

STATEMENTS OF INVENTION

According to a first aspect of the invention there is therefore provided a genetically transformed or transfected bacterial cell wherein said bacteria is able to invade human tissue and is characterised in that said bacterial cell is engineered to express siRNA active against at least one human gene encoding a cancer promoting or sustaining protein such as an oncogene, a chemo-resistant gene or a metabolic gene.

Reference herein to the term invade is reference to the ability of said bacterial cell to enter human cells.

In a preferred embodiment of the invention said bacterial cell is characterised in that it can colonise tumour cells in a preferential manner whereby the bacterial cell invades tumours cells in preference to healthy cells and, more ideally still, does so in a manner whereby, in ascending order of preference, there is a 10 fold, 100 fold or 1000 fold greater propensity to invade tumour tissues than healthy tissue (Hoffman, R M, 2011; Morrissey D, et al, 2010).

In yet a further preferred embodiment of the invention, said bacteria is selected from the genus *Salmonella* and, ideally an attenuated strain of *Salmonella* such as one commonly known to those skilled in the art, including, without limitation strain SL7207 (Hoiseth and Stocker 1981). However, in an alternative embodiment of the invention said bacterial cell may not be an attenuated strain, per se, but is made into an attenuated strain by the selective integration of nucleic acid, that encodes said siRNA, at sites that compromise the antigenicity or toxicity of said bacterial cell, but not its ability to thrive in a tumour environment, thus effectively attenuating same.

In yet a further preferred embodiment of the invention still, said oncogene is any known oncogene such as one commonly known to those skilled in the art, including, without limitation AR; C-MYC; BCL-2; and HER-2.

In yet a further preferred embodiment of the invention still, said chemo-resistance is any known chemo-resistance gene such as one or more commonly known to those skilled in the art, including, without limitation Mdr1.

In yet a further preferred embodiment of the invention said metabolic gene is poly ADP ribose polymerase (PARP) or pro-angiogenic growth factor genes (to target metastatic cells).

It therefore follows that the invention has application in the targeting of genes whose blocked expression has therapeutic value in terms of arresting the growth of, or shrinking, a solid tumour and/or making said tumour more susceptible to chemo-therapy.

Previous researchers using *Salmonella* SL7202 to deliver siRNA to cancer cells have used either (a) bacteria carrying a plasmid that is released into the cytoplasm and can replicate within the cancer cell and includes the genetic information for synthesis of the siRNA by the cancer cell itself, or (b) in the case of so-called 'trans-kingdom RNAi', bacteria carrying a multi-copy plasmid that directs synthesis of the siRNA within the bacteria, with the siRNA subsequently being released into the cytoplasm of the cancer cell. The current technology avoids use of any plasmid which can be lost at cell division in the absence of a selection pressure to maintain it.

The advantage of this approach, particularly in comparison with 'trans-kingdom RNAi', is that it provides for the long-term, sustainable delivery of siRNA to solid tumour in vivo.

In a preferred embodiment of the invention, said bacterial cell is transformed or genetically modified such that nucleic acid encoding said siRNA is stably integrated into the host cell chromosome. This advantageously ensures relatively long-term target gene silencing, in the order of weeks or months or throughout until the tumour shrinks. Ideally, stable chromosome integration is achieved by way of site specific integration in the host cell chromosome, typically following the use of conventional site specific integration sites, using techniques known to those skilled in the art such as, without limitation, lambda red recombination (Datsenko K A & Wanner B L (2000) One-step inactivation of chromosomal genes in *Escherichia coli* K-12 using PCR products Proc Natl Acad Sci USA. 97(12): 6640-6645) or RecA recombination.

In a preferred embodiment of the invention stable integration involves the use of about or a minimum of 36 nt regions, at either end of the cassette containing the siRNA, that are homologous to regions of the gene in which the cassette/siRNA is to be inserted, and possibly inactivated, this directs stable integration of the cassette into the targeted chromosomal locus (e.g. the rnc locus in *Salmonella*). More preferably 36, 37, 38, 39, 40, 41, 42, 43, 44, 45 46, 47, 48, 49 or 50 nt are used. More ideally still, one-step inactivation of the recombined gene is undertaken using Lambda Red recombination and so the phage Lambda Red recombinase, which is ideally synthesized under the control of a promoter, ideally inducible, on a plasmid, ideally an easily curable, low copy number plasmid. In the alternative a different type of recombination can be used such as RecA-mediated recombination. Whilst this other type of recombination tends to be less efficient, we compensate for this by using larger homologous regions at either end of the cassette. Thus, the homologous regions to the target gene that flank the cassette are approximately 1 kb or 1000 nt long.

It follows, that we prefer to use regions at either end of the cassette that have 100% identity with the region in the gene to be targeted or inactivated. This is because stable integration is important to ensure the siRNA remains in the host cell gene throughout the life of the cell and/or its progeny i.e. is stably inherited at cell division in the absence of any selection.

Yet more preferably we select the site where stable integration is to take place thus using a location within the bacterial chromosome so that the nucleic acid encoding said siRNA is stably inherited at cell division in the absence of any selection.

In a preferred embodiment of the invention, nucleic acid encoding said siRNA is integrated at a selected locus, such as one that promotes attenuation of said bacterial cell.

In the genus *Salmonella* we have integrated at the rnc locus because this prevents synthesis of RNaseIII which can potentially degrade siRNA, although other sites may be selected by those skilled in the art. Indeed, in a further preferred embodiment of the invention, we have integrated more than one nucleic acid molecule, or cassette, encoding more than one siRNA, wherein said multiple siRNAs are either different or the same thus allowing for multiple copies of the same siRNA or different siRNAs to be integrated into bacterial cell. Where multiple siRNAs are used we can speed up tumour clearance by targeting multiple genes etc. and reduce possible inflammatory side effects of the *Salmonella* by integrating the cassettes within specific bacterial genes.

In a preferred embodiment of the invention, said siRNA comprises a strand of RNA that shares 50% complementarity to at least one target gene and, in particular, the part of the gene that comprises one or more genetic mutations that is/are responsible for the cancer promoting properties of the gene. It is preferred that said siRNA comprises a strand of RNA that shares at least 75% complementarity to said gene and, in increasing order of preference, at least 80%, 85%, 90%, 91%, 92%, 93%, 94%, 95%, 96%, 97%, 98% or 99% complementarity to said gene.

In yet a further preferred embodiment of the invention, said transformed or transfected bacterial cell is also genetically engineered such that it does not produce functional RNA degrading proteins, including but not limited to, RNase I, RNase II, RNase III, RNase D, RNase E, RNase G, RNase P, RNase R, RNase T, RNase Z, RNase PH, RNase BN, RelE, MazF, Kid, PNPase, RhlB, enolase. Advantageously, this minimises the risk of enzymatic degradation of said siRNA encoded by the transformed bacterial cell. More ideally still, the nucleic acid encoding said siRNA is integrated into the gene encoding the afore RNA degrading proteins. As will be appreciated by those skilled in the art, such genetic recombination will permit synthesis of siRNA against the target gene whilst simultaneously preventing the production of functional RNA degrading proteins.

In yet a further preferred embodiment of the invention, said target gene is a gene involved in, but not limited to, growth or development. More preferably, said gene is such that its expression results in a solid tumour which provides an immune-suppressed/nutritional environment which *Salmonella* preferentially colonise.

Ideally said cancer is head/neck cancer, lung, liver, stomach, pancreatic, kidney, colon, rectal, ovarian, cervical, testicular, prostate, breast, colorectal or bone cancer.

In yet a further preferred embodiment of the invention, said siRNA is selected from the group comprising:

```
                                            (SEQ ID NO: 1)
          AAGAAGGCCAGTTGTATGGAC;

(SEQ ID NO: 2)
          GAGCAAGAAGATGAGGAAG;

(SEQ ID NO: 3)
          AACATCGCCCTGTGGATGACT;
```

-continued

AACAAAGAAATCTTAGACGAA; (SEQ ID NO: 4)

CGGCGCATAAGAAGCATAT; (SEQ ID NO: 5)

GTCCATACAACTGGCCTTCTT; (SEQ ID NO: 6)

CTTCCTCATCTTCTTGCTC; (SEQ ID NO: 7)

AGTCATCCACAGGGCGATGTT; (SEQ ID NO: 8)

TTCGTCTAAGATTTCTTTGTT
and (SEQ ID NO: 9)

ATATGCTTCTTATGCGCCG. (SEQ ID NO: 10)

According to a second aspect of the invention there is provided a vector wherein said vector comprises nucleic acid encoding i) siRNA active against at least one gene encoding a cancer promoting or sustaining protein such as an oncogene, a chemo-resistant gene or a metabolic gene; and ii) also nucleic acid encoding at least one selectable marker whose expression in the bacterial cell is indicative of the fact that the bacterial cell has been transformed or transfected with said siRNA.

In an alternative second aspect of the invention there is provided a non-replicating, ideally linear, nucleic acid molecule adapted to or able to integrate into a human tissue invading bacterial cell chromosome wherein said molecule comprises nucleic acid encoding i) siRNA active against at least one gene encoding a cancer promoting or sustaining protein such as an oncogene, a chemo-resistant gene or a metabolic gene; and, optionally, ii) also nucleic acid encoding at least one selectable marker whose expression in the bacterial cell is indicative of the fact that the bacterial cell has been transformed or transfected with said nucleic acid molecule.

In a preferred embodiment of the second aspect of the invention said siRNA is preceded by a promoter to enable the expression of said siRNA. Ideally said promoter is a bacterial promoter that is active in bacterial cells that replicate within a tumour cell, including but not limited to the pTAC promoter.

More preferably still, said vector includes at least one restriction site for insertion of siRNA cassette sequences by DNA cloning techniques, including but not limited to at least one AvrII restriction site or at least one MfeI restriction site, Ideally, said plasmid comprises a plurality of said restrictions sites and ideally two such sites, in use, one located either side of said siRNA and its associated transcription machinery.

More ideally still, said vector comprises spacer sequence located between a sense and anti-sense strand of said siRNA, most ideally yet said spacer sequence forms a loop sequence.

In yet further preferred embodiments of the invention said vector comprises at least one sequence selected from the group comprising:

(SEQ ID NO: 11)
GGTGGTCCTAGGGAGCTGTTGACAATTAATCATCGGCTCGTATAATGTGT

GGAATTGTGAAGAAGGCCAGTTGTATGGACTTCAAGAGAATATGCTTCTT

ATGCGCCGTTTTTCAATTGGGTGGT;

(SEQ ID NO: 12)
GGTGGTCCTAGGGAGCTGTTGACAATTAATCATCGGCTCGTATAATGTGT

GGAATTGTGAAGAGCAAGAAGATGAGGATTCAAGAGACTTCCTCATCTTC

TTGCTCTTTTTCAATTGGGTGGT;

(SEQ ID NO: 13)
GGTGGTCCTAGGGAGCTGTTGACAATTAATCATCGGCTCGTATAATGTGT

GGAATTGTGAACATCGCCCTGTGGATGACTTTCAAGAGAAGTCATCCACA

GGGCGATGTTTTTTCAATTGGGTGGT;

(SEQ ID NO: 14)
GGTGGTCCTAGGGAGCTGTTGACAATTAATCATCGGCTCGTATAATGTGT

GGAATTGTGAACAAAGAAATCTTAGACGAATTCAAGAGATTCGTCTAAGA

TTTCTTTGTTTTTTCAATTGGGTGGT;
and (SEQ ID NO: 15)
GGTGGTCCTAGGGAGCTGTTGACAATTAATCATCGGCTCGTATAATGTGT

GGAATTGTGCGGCGCATAAGAAGCATATTTCAAGAGAATATGCTTCTTAT

GCGCCGTTTTTCAATTGGGTGGT.

According to a third aspect of the invention, there is provided the afore described bacterial cell for use in a method for treating cancer.

According to a fourth aspect of the invention, there is provided the use of the afore described bacterial cell in the manufacture of a medicament to treat cancer.

In a preferred embodiment of the third or fourth aspect of the invention said cancer is a solid tumour, ideally, as afore described.

In the claims which follow and in the preceding description of the invention, except where the context requires otherwise due to express language or necessary implication, the word "comprises", or variations such as "comprises" or "comprising" is used in an inclusive sense i.e. to specify the presence of the stated features but not to preclude the presence or addition of further features in various embodiments of the invention.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

Figure 1B:
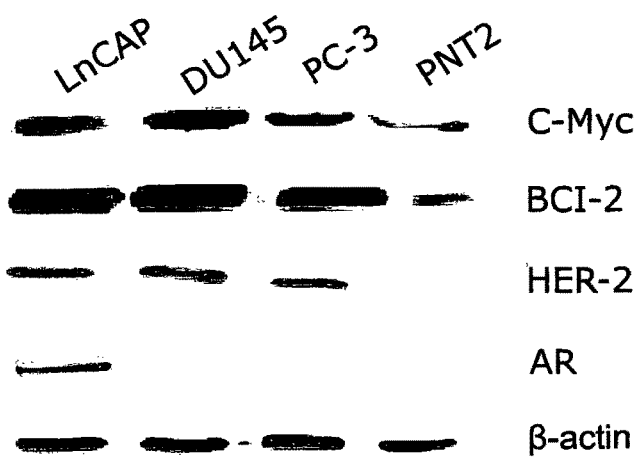

The present invention will now be described by way of example only with particular reference to the following figures wherein:

FIGS. 1A-1B. Analysis of target genes by A; QRT-PCR and B; Western Blot. RNA was isolated from the four cell types and relative expression levels of the oncogenes c-myc, bcl-2, Her-2 and androgen receptor were detected with qRT-PCR (real time, reverse transcription PCR) and protein levels were assessed by Western blot. All oncogenes were over-expressed relative to the housekeeping genes; HPRT and Beta actin and compared to the non-cancerous cell lines; PNT2. The expression of c-myc was found to be significantly higher in the 3 cancer cell lines compared to PNT2 (P=≤0.05 as indicated by '*') similarly with BCl-2. LnCap showed significantly higher expression of HER-2 as did PC-3 and LnCap cells also over-expressed Androgen Receptor. Results represent the mean of triplicate data and error bars represent standard deviation. Statistical significance was determined using the Students t-test in R software.

Figure 2A:
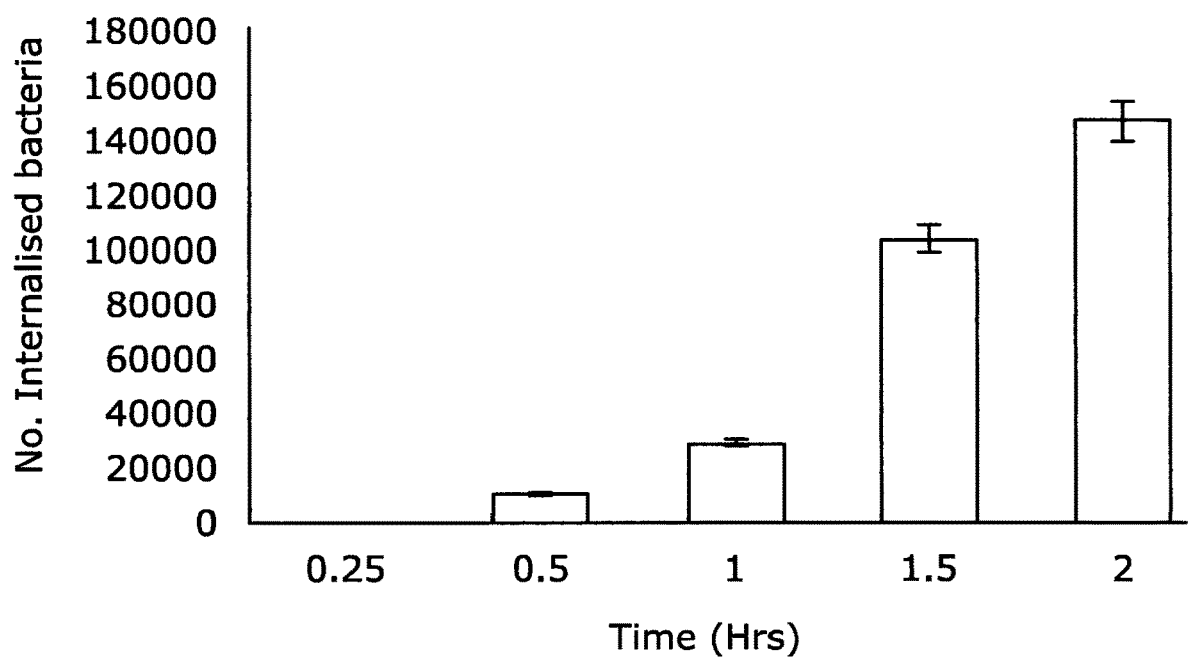
Figure 2B:
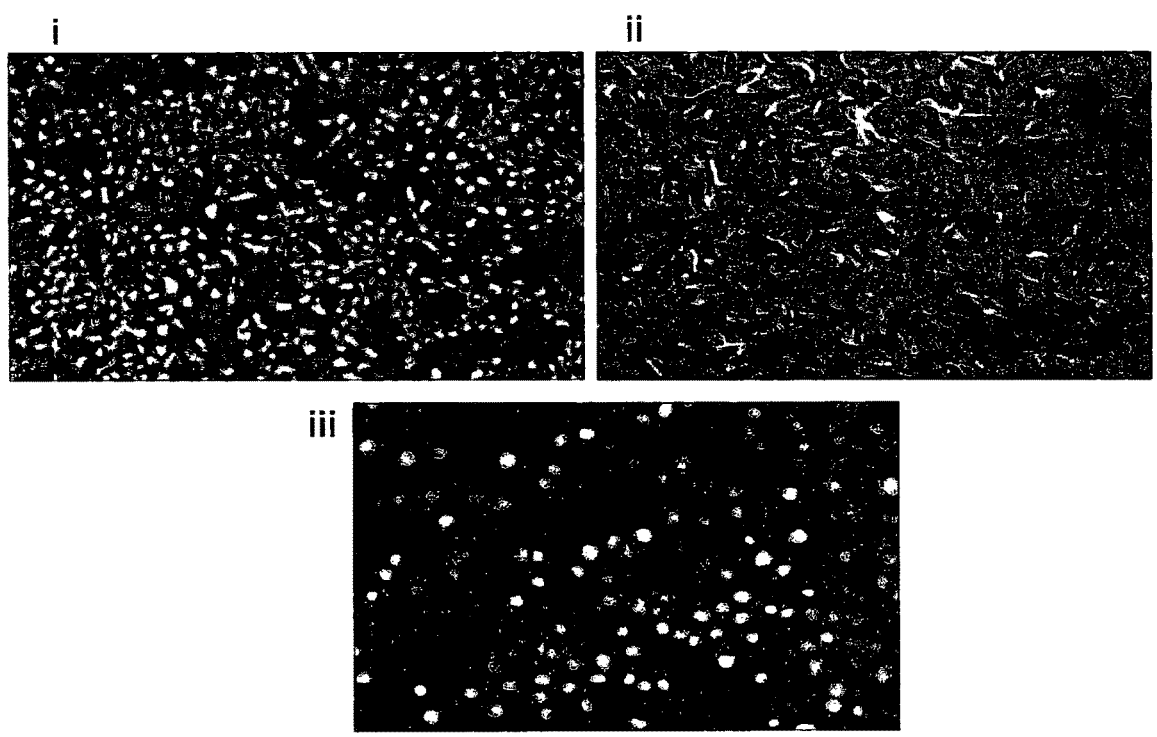

FIGS. 2A-2B. Intracellular invasion assay. A; Bacteria were found to have invaded PC-3 cells after 30 min and the number of intracellular bacteria increased with time. Results represent the mean of triplicate data B; PC-3 cells before (B i) S. typhimurium SL7027 expressing GFP (B ii) and PC-3 cells fluorescing green after incubation with S. typhimurium SL7027 expressing GFP (B iii).

Figure 3:
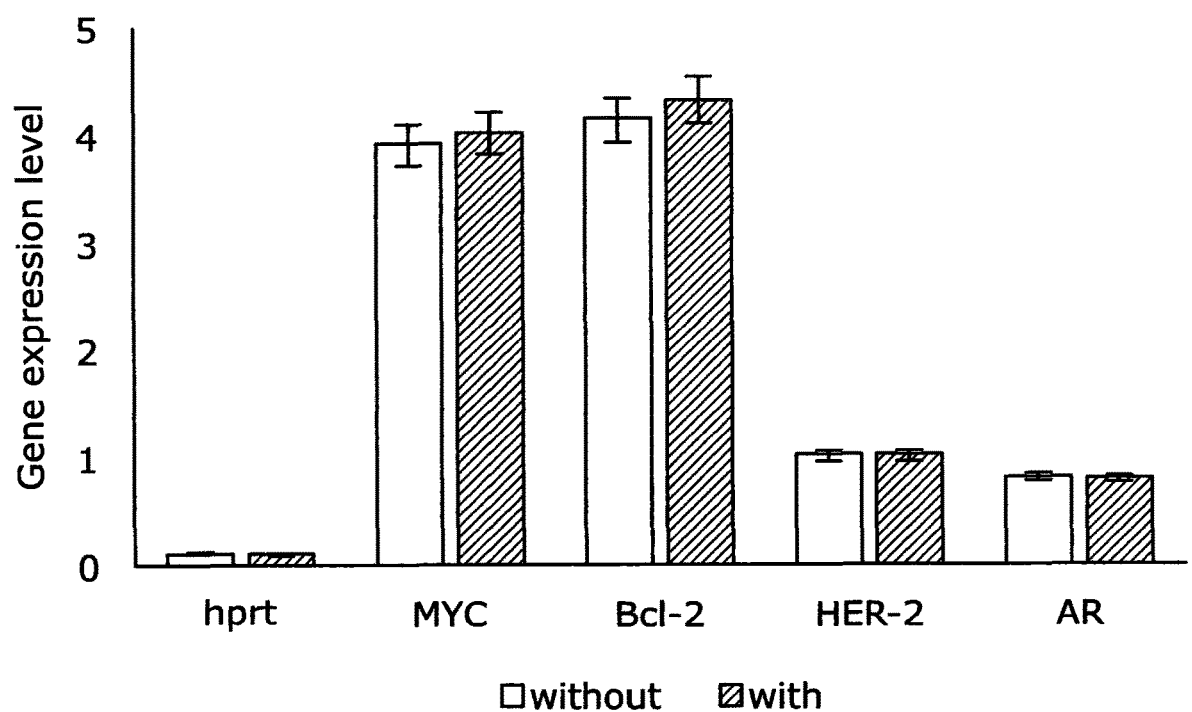

FIG. 3. Co-culture with S. typhimurim SL7207 does not alter gene expression. Cell lines were co-cultured with S. typhimurim SL7207 as previously described. RNA was isolated after 24 hours of co-culture and the samples were subject to qRT-PCR to observe whether bacterial co-culture influenced gene expression and how this might impact future analysis investigating gene knockdown via bacterial delivery of siRNA. No significant difference were found for any of the oncogenes nor housekeeping genes and it was concluded that co-culture did not alter our target gene expression and this would not affect siRNA analysis in the future.

Figure 4A:
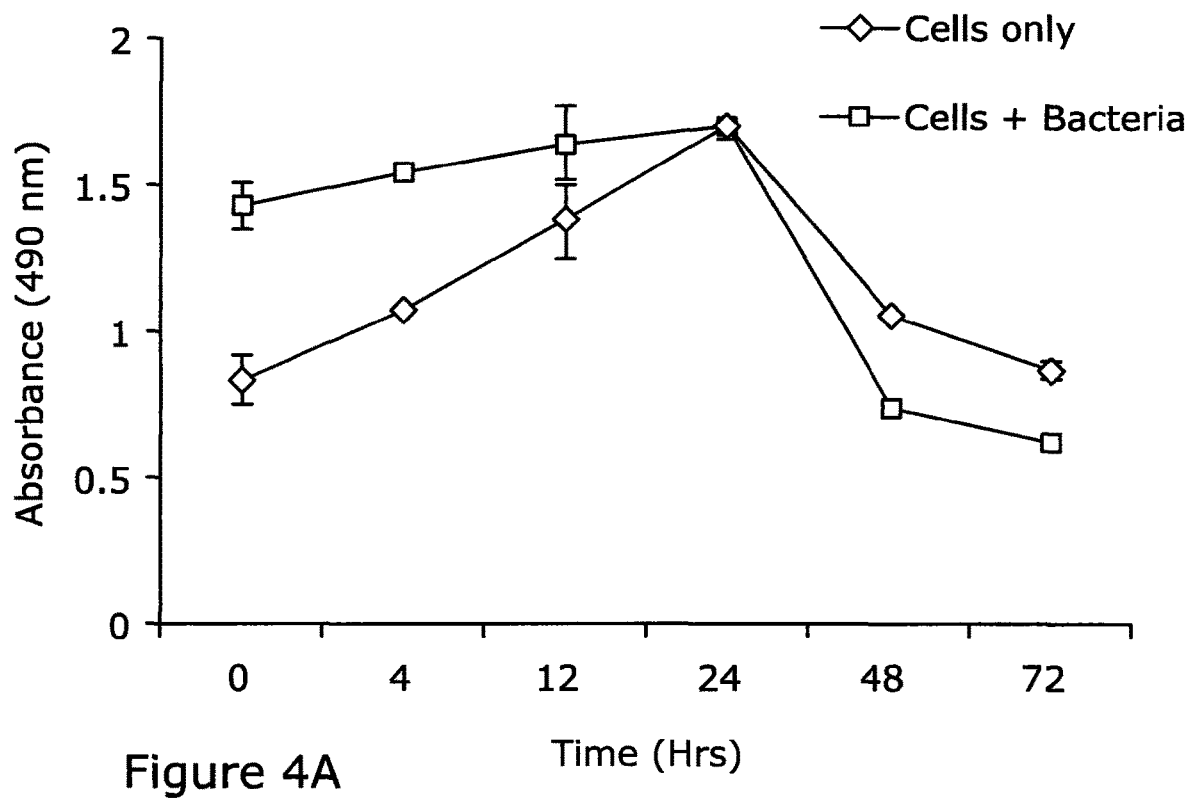
Figure 4B:
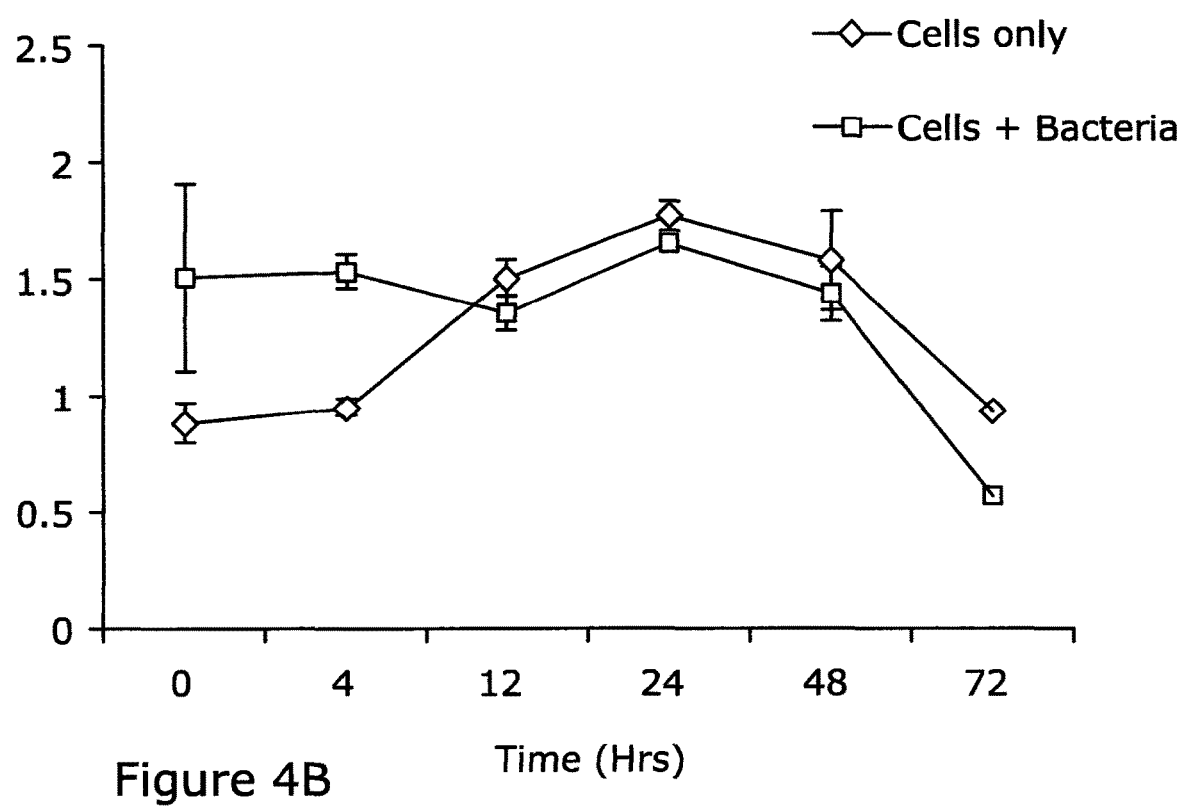
Figure 5D:
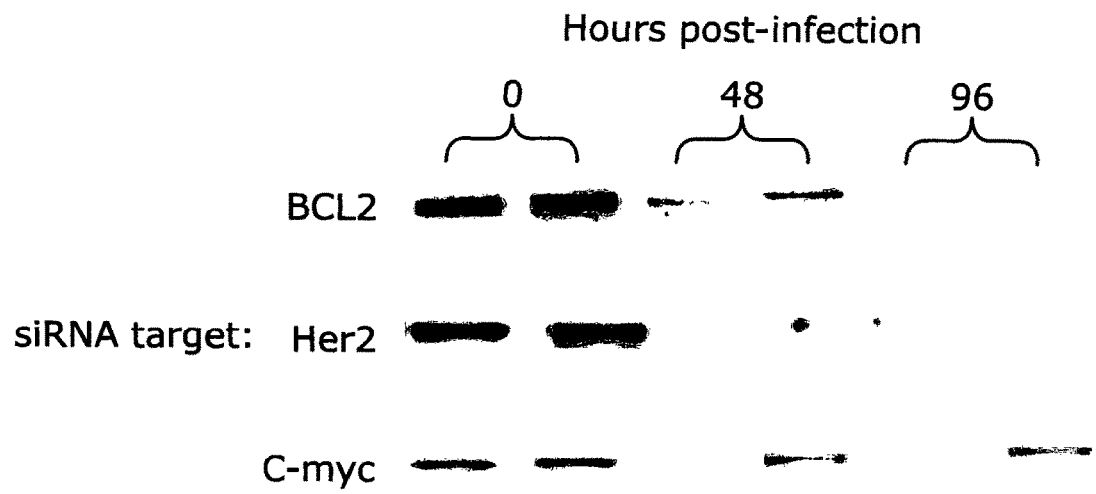

FIGS. 4A-4B. Cell proliferation assay with and without bacterial invasion. A; PC-3 and, B; PNT2 cell lines were subject to the CellTiter 96® Aqueous One Solution Cell Proliferation assay (Promega) according to the manufactures' instructions with the addition of bacteria to one plate ('with' bacteria 96-well plate). Cell viability began to decline following 48 hr incubation however co-culture had no effect on cell proliferation for either cell line. Results represent the mean of triplicate data and error bars represent standard deviation.

FIGS. 5A-5D Effect of siRNA on target gene expression. RNA was isolated from PC-3 cells following incubation with and without bacteria carrying the siRNA cassette targeting BCL2 (A), C-MYC (B) and Her2 (C) at time 0, after, 48 and 96 hours post-infection. Relative expression levels of the oncogenes c-myc, bcl-2 and Her-2 were detected with qRT-PCR. In the presence of bacteria harbouring the siRNA cassette, the expression of all 3 oncogenes were significantly reduced after 48 and 96 hours post-infection. ($P=\leq 0.05$ as indicated by '*'). Results represent the mean of triplicate data and error bars represent standard deviation. Statistical significance was determined using the Students t-test in R software. Protein expression by target oncogenes was also monitored by Western blot and revealed protein expression was diminished after 48 hours and 96 hours post-infection.

Figure 6:
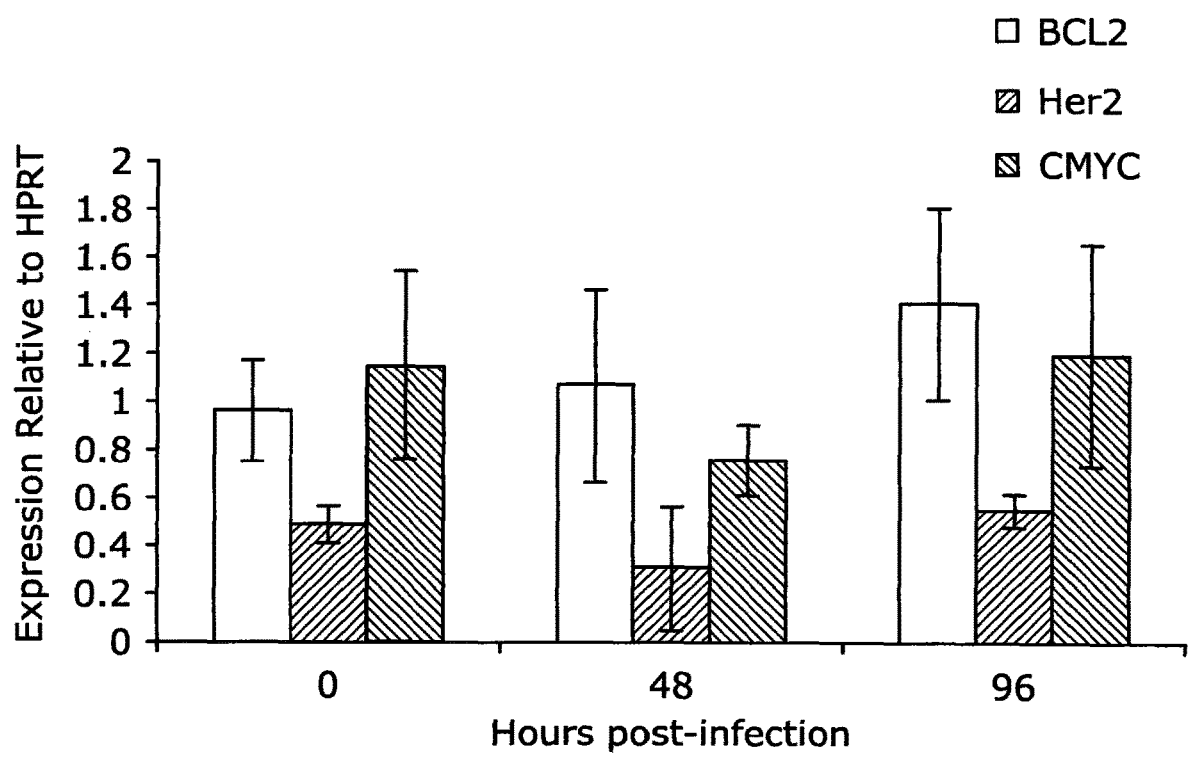

FIG. 6. The effect of siRNA negative control on the expression of target oncogenes. No significant change in the expression of the oncogenes was observed after infection with bacteria expressing siRNA Negative.

Figure 7:
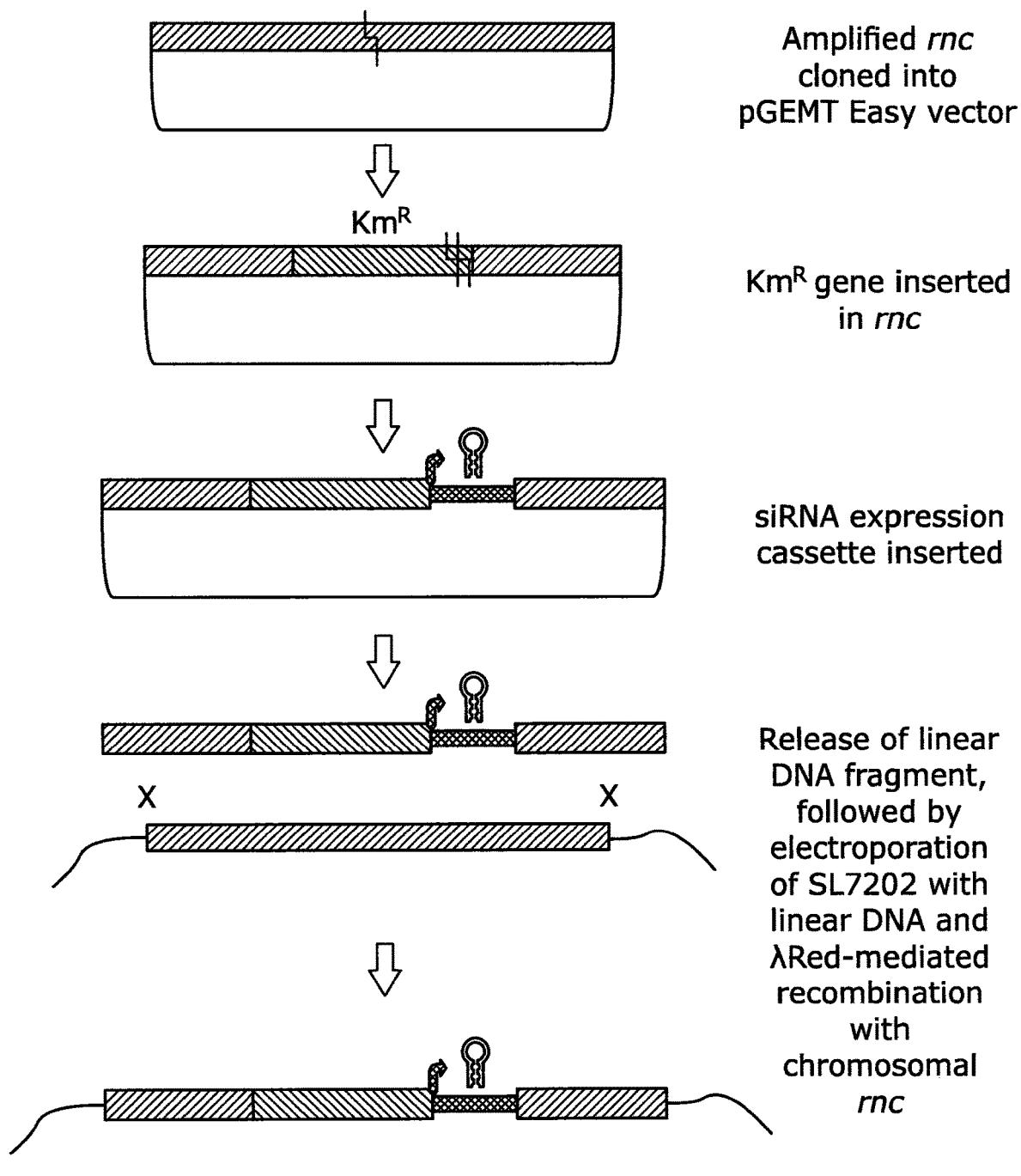

FIG. 7. Strategy for chromosomal integration of siRNA cassette exemplified by integration at the rnc locus (⌐⌐⌐⌐⌐⌐=restriction site); a suitable vector is made containing the siRNA expression cassette and this is cut out and electroporated into the selected strain of salmonella.

Figure 8:
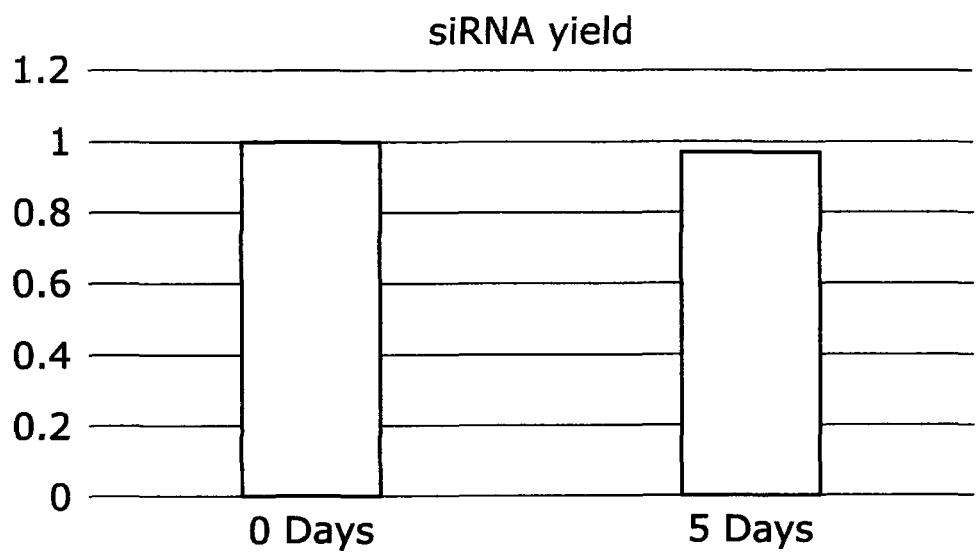

FIG. 8. Comparison of relative siRNA yields from S. tymphimurium SL7202 with a chromosomally integrated siRNA expression cassette from cultures grown at t=0 and after 5 days non-selective subculture (t=5 days).

Figure 9:
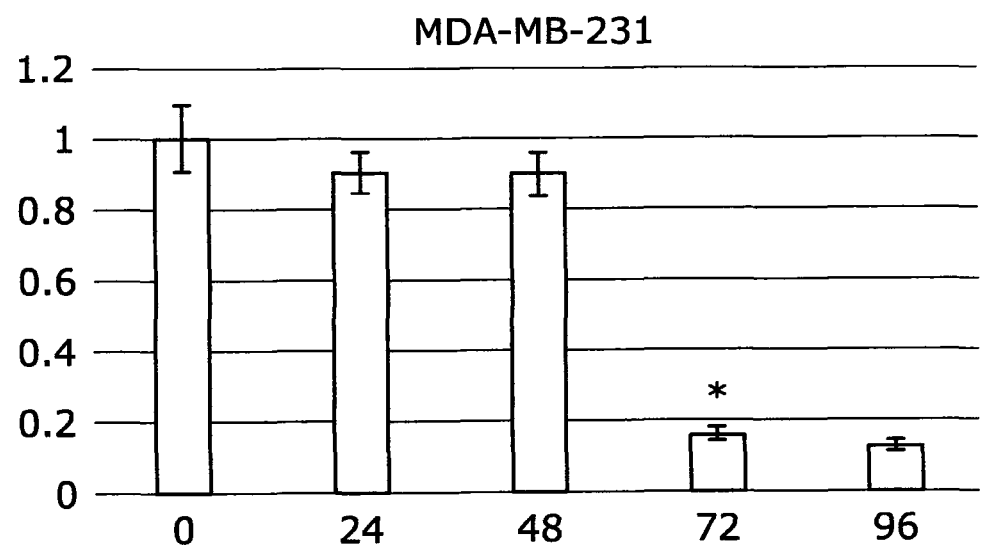

FIG. 9. RNAi of c-Myc in metastatic human breast adenocarcinoma cells ($P=\leq 0.05$ as indicated by '*').

Figure 10:
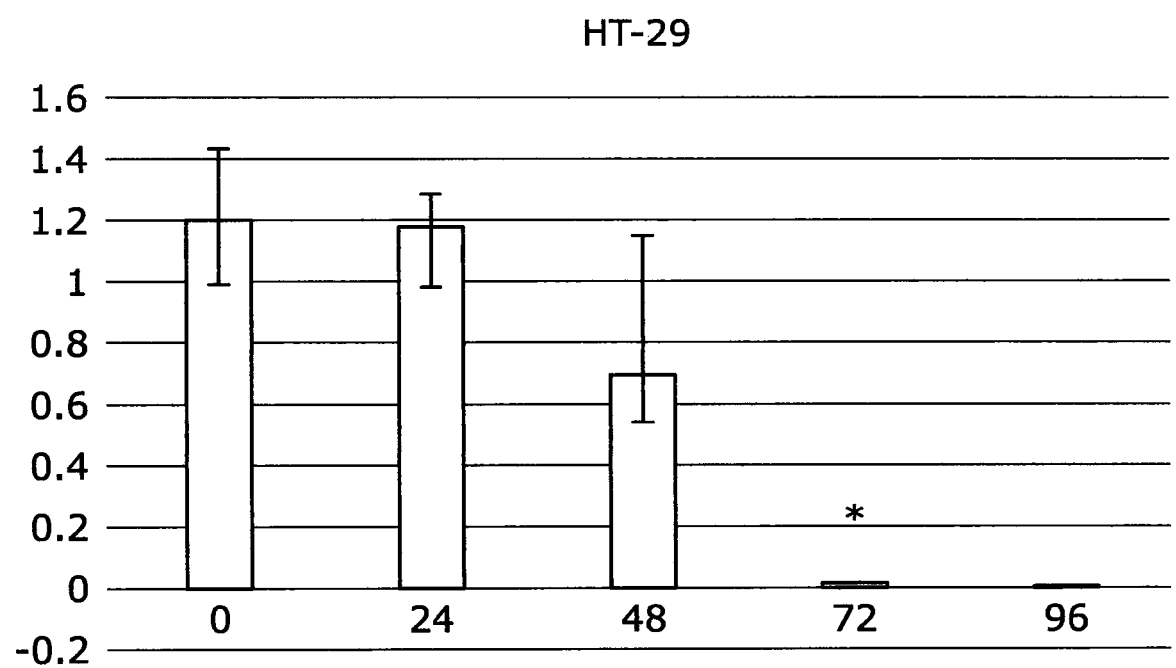

FIG. 10. RNAi of c-Myc in human colorectal adenocarcinoma cells ($P=\leq 0.05$ as indicated by '*').

MATERIALS AND PROCEDURE

Bacteria, Plasmids and Culture Conditions

The bacterial strains and plasmids used, along with their growth requirements and the chapters to which they are relevant are indicated in Table 1.1.

Table 1 Bacterial strains, growth conditions and plasmids used in this thesis. TSA: Tryptone soy agar, Amp: Ampicillin, Cm: Chloramphenicol, Km: Kanamycin.

Handling of Frozen Cell Suspension and Preparation of Initial Low Density Cell Stock Frozen vials of the human prostate cancer cell lines PC-3, DU145 and LNCaP and the normal prostate cell line PNT2 were stored in the vapour phase of liquid nitrogen. For preparation of initial cell stock, a vial was rapidly thawed (approximately 1 min) with gentle agitation in a 37° C. water bath while keeping the 'O-ring' and cap out of the water to reduce the possibility of contamination. The vial was sterilised decontaminated by spraying with 70% ethanol and transferred to a BSL-2 aseptic laminar flow hood where all proceeding operations were carried out. The vial's contents were transferred to a centrifuge tube containing 10 mL complete culture medium which comprised; RPMI 1640 medium (Life technologies) supplemented with 10% fetal bovine serum (FBS) and 5% penicillin-streptomycin solution (ATCC®, Middlesex, UK) and centrifuged at approximated 125×g for 8-10 min. The resultant pellet was resuspended in complete growth medium and 1 mL cell suspension was removed for cell count and viability performed using a haemocytometer. The cells were dispensed into a T-25 cm$^2$ culture flask (Corning Life Sciences, Amsterdam, The Netherlands) at a cell density of approximately $1.6 \times 10^5$ cells/cm$^2$. Cells were routinely maintained at 37° C. in 5% CO$_2$ atmosphere in a suitable incubator. Cells were observed daily under an inverted microscope to ensure the culture was not contaminated and were sub-cultured upon reaching 50% confluence (approximately $5.5 \times 10^4$ cells).

Cell Line Maintenance and Sub-Culturing Procedure

After growing the cells overnight the medium was removed from the culture flask and cells were washed with 2 mL Dulbecco's phosphate buffered saline (Life Technologies) and 2 mL 0.25% (w/v) Trypsin-0.53 mM EDTA solution (ATCC®) was added quickly after washing. Cells were observed under an inverted microscope for cell layer dispersion, if cells were difficult to detach, flasks were incubated at 37° C. for 5-15 min. Fresh complete growth medium (6 to 8 mL) was added to the flasks and cells were aspirated with gently pipetting. Appropriate aliquots of the cell suspension (using a sub-cultivation ratio of 1:10 to 1:12) were added to new culture vessels and incubated at 37° C. in 5% CO$_2$ atmosphere.

Cryopreservation

Cells were harvested as described in sub-culturing procedure. Prior to cell detachment, the cryopreservation medium was prepared as follows; complete growth medium was supplemented with 5% (v/v) DMSO and kept on ice until use. Cell density and viability was recorded and the cells were centrifuged at 125×g for 5 min at room temperature. The media was carefully removed by using an automatic pipette to leave the cell pellet. Cryopreservation media was added so as to achieve a cell density of between $3.0 \times 10^6$ to $4.0 \times 10^6$ cells/mL and cells were resuspended with gentle pipetting. Cells were dispensed in 1 mL aliquots into cryovials (Thermo-Scientific) and equilibrated at 4° C. for a maximum time of 10 min.

The day prior to cell cryopreservation, 250 mL isopropanol (Sigma-Aldrich) was added to a freezing container (Sigma-Aldrich) and placed at 4° C. overnight. On the day of cryopreservation, after equilibration at 4° C. cryovials were inserted into the passive freezer and transferred to a −80° C. freezer and left overnight. The next day the cryovials were transferred to the vapour phase of a liquid nitrogen freezer.

Intracellular Growth Assay and Morphology

Briefly, 1×10$^5$ prostate cancer cells were seeded onto cover slips in a 24-well plate and seeded to 30% confluency (~overnight). Media was removed and replace with anitbiotic free media and cells were infected with 20 bacteria per cell (MOI 20) for 2 hrs at 37° C. The medium was replaced with RPMI 1640 supplemented with 100 µg/ml gentamicin to kill extracellular bacteria and incubated for a further 1 hr. To monitor intracellular growth prostate cancer cells were disrupted using 1% saponin in PBS for 10 min at 37° C. at different time points (0, 2, 4, 6, 8 and 24 hours post extracellular bacterial killing) to release intracellular bacteria. Samples were diluted in PBS and plated on TSA plates for determination of the recovered colony forming units (cfu).

To monitor the effects of bacterial infection on cell line morphology, the above experiment was conducted except without the cellular disruption step. Instead, after each incubation time, cover slips were washed and mounted for observation with the microscope.

qPCR qPCR Primers for the target oncogenes are shown in Appendix table 3

Proliferation Assay

PC-3 and PNT2 cell lines were subject to the CellTiter 96® Aqueous One Solution Cell Proliferation assay (Promega) per the manufactures' instructions with or without the addition of bacteria.

Construction of siRNA Cassette and Stable Integration into Bacterial Chromosome

The rnc gene (RNAseIII encoding gene) of *S. typhimurium* SL7207 was amplified by PCR (2× MangoMix (Bioline, London, UK), 4 µM Forward primer 4 µM Reverse Primers, ddH2O)) (Primer sequences are shown in Appendix table 1). PCR product was cleaned using PCR clean-up kit (QIAGEN, Manchester, UK) per the manufacturer's instructions and then cloned into pGEM® t-Easy vector (Promega) (*E. coli* JM109 was used as a host for most genetic manipulation steps). Positive clones were selected and subject to plasmid preparations. The rnc gene within the plasmid was digested using BssHII restriction enzyme and the plasmid was blunt ended and dephosphorylated. The Kanamycin resistance gene from pCR2.1 was also amplified by PCR using a polymerase that generated blunt ends (NEB Phusion® polymerase and the primers in appendix table 2. This PCR product was cleaned and phosphorylated and cloned into the pGEM® T-Easy-RNC vector. Positive clones were selected based upon their ability to grow on ampicillin and Kanamycin agar plates. The Kanamycin forward primer was designed to include two restriction enzyme sites (AvrII and MfeII) to allow double digest and directional insertion of the siRNA cassettes which also included these restriction site sequences. The siRNA cassettes plasmids were subject to double digests with AvrII and MfeII to release the cassette sequences. The cassettes were cloned into pGEM-TEasy-RNC-KM AvrII and MfeII double digested plasmids and transformed into *E. coli*. Positive clones were selected and subject to EcoRI digests to release the siRNA cassettes together with flanking rnc and KmR gene sequences. These linear DNAs were introduced into SL7207 together with the Lambda Red recombination plasmid pKD46. Positive clones were selected and used for Lambda red recombination of the siRNA cassettes into the chromosomal rnc gene.

Stability of siRNA Expression in *S. typhimurium* SL7202

The current technology avoids the use of any plasmid that can be lost at cell division in the absence of a selection pressure to maintain it by using a chromosomally-integrated cassette. This approach provides for the long-term, sustainable delivery of siRNA to solid tumour in vivo. To measure plasmid stability in vitro and to confirm the stability of siRNA synthesis we undertook the following experiments.

Methods

Bacterial Strains:

(1) *S. tymphimurium* SL7202 with a siRNA expression cassette and kanamycin resistance gene stably integrated into the bacterial chromosome at the rnc locus

```
(siRNA negative control sequence cassette:
GGTGGTCCTAGGGAGCTGTTGACAATTAATCATCGGCTCGTATAATGTGT

GGAATTGTGCGGCGCATAAGAAGCATATTTCAAGAGAATATGCTTCTTAT

GCGCCGTTTT TCAATTGGGTGGT, SEQ ID NO: 15).
```

(2) *S. tymphimurium* SL7202 carrying plasmid pME6 (Fernadez-Martinez et al [2009] Osmoregulation in *Streptomyces coelicolor*: modulation of SigB activity by OsaC. Mol Microbiol doi: 10.1111/j.1365-2958.2009.06599.x) that contains the same kanamycin resistance gene.

shRNA synthesis was determined after extraction of RNA and qRT-PCR using primers:

```
                                          (SEQ ID NO: 16)
      Forward 5'  GGTGGTCCTAGGGAGCTGTT (SEQ ID NO: 17)
      Reverse 5'  CCCAATTGAAAAACGGCGCAT
```

RNAi of c-Myc in Breast and Colorectal Cancer Cells

The data to demonstrate RNAi of oncogenes delivered by our technology focussed in FIGS. 1-6 on prostate cancer cell lines. To extend this, we have now employed the technology to target c-Myc expression in both breast and colorectal cancer cells.

Methods

*S. tymphimurium* SL7202 with a siRNA expression cassette stably integrated into the bacterial chromosome at the rnc locus targeting c-Myc (siRNA cassette sequence: GGTGGTCCTAGGGAGCTGTTGACAATTAATCATCG-GCTCGTATAATGTGTGGAA TTGTGAAGAGCAAGA-AGATGAGGATTCAAGAGACTTCCTCATCTTCTTGC-TCTTT TTCAATTGGGTGGT, SEQ ID NO: 12), was used to infect cell lines. mRNA was extracted periodically and the abundance of c-Myc mRNA was determined by qRT-PCR using primers:

```
                                          (SEQ ID NO: 18)
      Forward: 5'  GAGCAAGAAGATGAGGAAG (SEQ ID NO: 19)
      Reverse: 5'  CTTCCTCATCTTCTTGCTC
```

Results

FIG. 1 demonstrates that, in relation to a normal cell line PNT2, several oncogenes and the androgen receptor (AR) are over-expressed in cultured prostate tumour cell lines (PC-3, LNCaP and DU145). This was determined at the level of transcript abundance (panel A), using quantitative real-time PCR, and also by visualising the abundance of the respective proteins (panel B) by Western blotting. The complementary data indicate over-expression of C-MYC and Bcl-2 in all 3 tumour cell lines, over-expression of Her-2 in the PC-3 and LNCaP cell lines, and over-expression of androgen receptor in LNCaP cells.

To quantify the ability of *Salmonella* strain SL7207 to invade human cells grown in culture, a derivative of SL7207 expressing green fluorescent protein (eGFP) was engineered. These bacteria were incubated with PC-3 cells and cell invasion quantified (FIG. 2 A), indicating measurable invasion within 30 minutes and subsequent rapid multiplication of intracellular bacterial cell numbers until 2 hours post-infection. The intracellular bacteria were visualised using fluorescence microscopy (FIG. 2 B).

To ensure measurable RNAi effects could not be attributed to cell infection by SL7207 not expressing siRNA, transcript abundance for target genes and a housekeeping gene was quantified in the PC-3 cell line with and without infection (FIG. 3). The results indicate that bacterial infection alone has no effect on transcript abundance. Moreover, we also determined that bacterial infection has no significant effect on short-term cell viability (FIG. 4). PC-3 (panel A) and PNT2 (panel B) cell viability was measured over 72 h with and without infecting SL7207 bacteria.

RNAi after infection with SL7207 strains expressing the relevant siRNA was exemplified in PC-3 cells in the case of Bcl-2 (FIG. 5 A), C-MYC (FIG. 5B) and Her2 (FIG. 5C), both at the level of transcript abundance, as determined by qRT-PCR, and protein level (FIG. 5D) using Western blotting. Significant reductions in transcript abundance, reflected in protein levels, were observed 48 h post-infection, that continued until the end of the experiment (96 h post-infection). The specificity of RNAi was confirmed by infection of PC-3 cells with SL7207 expressing an off-target siRNA (FIG. 6): no significant changes in the abundance of the target gene transcripts were observed over the 96 h period post-infection.

FIG. 7 is a graphical representation for the strategy to engineer the siRNA expression cassette so that it is integrated within the rnc gene in the chromosome of SL7207. As a consequence, the siRNA is continuously synthesised by the bacteria in the absence of antibiotic selection and is released into a tumour cell when the bacterial cell dies.

Stability of siRNA expression in *S. typhimurium* SL7202 was investigated and the results are shown in FIG. 8. Cultures of the two strains (1) and (2) described above were grown in LB medium without antibiotic selection (to mimic growth conditions in cellulo/in vivo) for 5 days, sub-culturing every 12 h. Kanamycin resistant cells were quantified as a proportion of total cell number on each day of subculture. After 5 days, 98-100% of cells of culture (1) retained kanamycin resistance, whereas only 2.3% (+/− 1.4%) of cells of culture (2) retained kanamycin resistance.

siRNA synthesis in culture (1) was quantified, comparing yields prior to sub-culturing (t=0) and at the end of sub-culturing (t=5 days). There was no significant difference in siRNA yields comparing data from cultures sampled at t=0 and t=5 days (FIG. 8).

Very significant reductions in c-Myc mRNA due to RNAi were observed after 72 h infection in both breast (FIG. 9) and colorectal (FIG. 10) cancer cell lines.

TABLE 1

Bacterial strains, growth conditions and plasmids used in this thesis.

| Species/Plasmid | Use | Media | Temp | Antibiotic |
|---|---|---|---|---|
| *S. typhimurium* SL7202 | Host strain for all genetic manipulations | TSA | 37 | — |
| *S. typhimurium* SL7207 GFP | Host strain expressing GFP plasmid | TSA | 37 | Amp (100 µg/ml) |
| *S. typhimurium* SL7207 mCherry | Host strain expressing mCherry plasmid | TSA | 37 | Amp (100 µg/ml) |
| *S. typhimurium* SL7207 AR siRNA plasmid | Host strain expressing plasmid with AR siRNA cassette plasmid | TSA | 37 | Amp (100 µg/ml) |
| *S. typhimurium* SL7207 C-myc siRNA plasmid | Host strain expressing plasmid with c-myc siRNA cassette plasmid | TSA | 37 | Amp (100 µg/ml) |
| *S. typhimurium* SL7207 Her2 siRNA plasmid | Host strain expressing plasmid with her2 siRNA cassette plasmid | TSA | 37 | Amp (100 µg/ml) |
| *S. typhimurium* SL7207 Bcl2 siRNA plasmid | Host strain expressing plasmid with bcl2 siRNA cassette plasmid | TSA | 37 | Amp (100 µg/ml) |
| *S. typhimurium* SL7207 Neg siRNA plasmid | Host strain expressing plasmid with neg siRNA cassette plasmid | TSA | 37 | Amp (100 µg/ml) |
| *S. typhimurium* SL7207 AR | Host strain with AR cassette integrated into chromosome | TSA | 37 | Amp (100 µg/ml) |
| *S. typhimurium* SL7207 c-myc | Host strain with cmyc cassette integrated into chromosome | TSA | 37 | Amp (100 µg/ml) |
| *S. typhimurium* SL7207 Her2 | Host strain with Her2 cassette integrated into chromosome | TSA | 37 | Amp (100 µg/ml) |
| *S. typhimurium* SL7207 Bcl2 | Host strain with Bcl2 cassette integrated into chromosome | TSA | 37 | Amp (100 µg/ml) |
| *S. typhimurium* SL7207 neg | Host strain with neg cassette integrated into chromosome | TSA | 37 | Amp (100 µg/ml) |
| *E. coli* JM109 pME6 | *E. coli* competent strain harbouring pME6 plasmid which has the Kanamycin gene | TSA | 37 | Amp (100 µg/ml) Km (50 µg/ml) |
| *E. coli* JM109 pGEM-rnc | *E. coli* harbouring pGEM-rnc | TSA | 37 | Amp (100 µg/ml) |
| *E. coli* JM109 pGEM-rnc-Km | *E. coli* harbouring pGEM-rnc-Km | TSA | 37 | Amp (100 µg/ml) Km (50 µg/ml) |
| *S. typhimurium* SL7207 pKD46 | Host strains harbouring pKD46 Lambda Red recombination plasmid | TSA | 30 | Amp (100 µg/ml) |

TSA: Tryptone soy agar, Amp: Ampicillin, Cm: Chloramphenicol, Km: Kanamycin.

TABLE 1

RNAseIII primers sequences

| Primer | Sequence |
|---|---|
| RNAse III gene (rnc) Forward | GACGATGGCAATAAATCCGCAG (SEQ ID NO: 20) |
| RNAse III gene (rnc) Reverse | TCGTGTGCTGGATTGTTGAC (SEQ ID NO: 21) |

TABLE 2

Primer Sequences for amplification of the Kanamycin gene. Restriction enzymes sites AvrII (shown in italics - 1st underlined section) and MfeI (bold - second underlined section) are also shown.

| Primer | Sequence |
|---|---|
| Kanamycin Forward | GGTGGT*CCTAGG*GTGGTCAATTGCGGTTT (SEQ ID NO: 22) |
| Kanamycin Reverse | GAATACTCATACTCTTCCTT (SEQ ID NO: 23) |

TABLE 3

Primer sequences for target oncogenes for qPCR

| Gene | siRNA sequence sense strand | Reverse complement | Ref |
|---|---|---|---|
| AR | 5'-AAGAAGGCCAGTTGTATGGAC-3' (SEQ ID NO: 1); | GTCCATACAACTGGCCTTCTT (SEQ ID NO: 6) | [1] |
| C-MYC | 5'-GAGCAAGAAGATGAGGAAG-3' (SEQ ID NO: 2) | CTTCCTCATCTTCTTGCTC (SEQ ID NO: 7) | [2] |
| BCL-2 | 5'-AACATCGCCCTGTGGATGACT-3 (SEQ ID NO: 3) | AGTCATCCACAGGGCGATGTT (SEQ ID NO: 8) | [3] |
| HER-2 | 5'-AACAAAGAAATCTTAGACGAA-3' (SEQ ID NO: 4) | TTCGTCTAAGATTTCTTTGTT (SEQ ID NO: 9) | [4] |
| Negative Control | 5'-CGGCGCATAAGAAGCATAT-3' (SEQ ID NO: 5) | ATATGCTTCTTATGCGCCG (SEQ ID NO: 10) | [2] |

TABLE 4 siRNA cassette sequences for the target oncogenes.

| siRNA Target gene | Sequence |
|---|---|
| AR | GGTGGTcctagg<u>GAGCTGTTGACAATTAATCATCGGCTCGTATAATGTGTGGAATTGTGA</u>AGAAGGCCAGTTGTATGGAC*TTCAAGAG*AATATGCTTCTTATGCGCCG TTTTTcaattgGGTGGT (SEQ ID NO: 11) |
| C-MYC | GGTGGTcctagg<u>GAGCTGTTGACAATTAATCATCGGCTCGTATAATGTGTGGAATTGTGA</u>AGAGCAAGAAGATGAGGA*TTCAAGAGA*CTTCCTCATCTTCTTGCTC TTTTTcaattgGGTGGT (SEQ ID NO: 12 |
| BCL2 | GGTGGTcctagg<u>GAGCTGTTGACAATTAATCATCGGCTCGTATAATGTGTGGAATTGTGA</u>ACATCGCCCTGTGGATGACT*TTCAAGAG*AAGTCATCCACAGGGCGATGT TTTTTTcaattgGGTGGT (SEQ ID NO: 13) |
| HER2 | GGTGGTcctagg<u>GAGCTGTTGACAATTAATCATCGGCTCGTATAATGTGTGGAATTGTGA</u>ACAAAGAAATCTTAGACGAA*TTCAAGAG*ATTCGTCTAAGATTTCTTTGT TTTTTTcaattgGGTGGT (SEQ ID NO: 14) |
| NEGATIVE | GGTGGTcctagg<u>GAGCTGTTGACAATTAATCATCGGCTCGTATAATGTGTGGAATTGTGA</u>CGGCGCATAAGAAGCATAT*TTCAAGAGA*ATATGCTTCTTATGCGCCGT TTTTcaattgGGTGGT (SEQ ID NO: 15) |

The lower case sequence shows the AvrII restriction site, the lower case bold sequence shows the MfeI site. The pTAC promoter sequence is underlined, the sense and antisense RNAi encoding region are shown in large font, separated by the loop sequence which is shown in italics and followed by a poly T transcriptional terminating sequence.

TABLE 5

Primer Sequences for siRNA expression from *S. typhimurium* mutants

| AR | Sequence (5'→3') | Length | Start | Stop | Tm | GC % |
|---|---|---|---|---|---|---|
| Forward primer | GGTGGTCCTAGGGAGCTGT (SEQ ID NO: 24) | 19 | 1 | 19 | 60.31 | 63.16 |
| Reverse primer | ACAACTGGCCTTCTTCACAATTC (SEQ ID NO: 25) | 23 | 74 | 52 | 59.68 | 43.48 |
| CMYC | Sequence (5'→3') | Length | Start | Stop | Tm | GC % |
| Forward primer | GGTCCTAGGGAGCTGTTGAC (SEQ ID NO: 26) | 20 | 4 | 23 | 59.46 | 60.00 |
| Reverse primer | CCACCCAATTGAAAAAGAGCA (SEQ ID NO: 27) | 21 | 122 | 102 | 57.25 | 42.86 |
| BCL2 | Sequence (5'→3') | Length | Start | Stop | Tm | GC % |
| Forward primer | GGTGGTCCTAGGGAGCTGT (SEQ ID NO: 28) | 19 | 1 | 19 | 60.31 | 63.16 |
| Reverse primer | ACAGGGCGATGTTCACAATTC (SEQ ID NO: 29) | 21 | 72 | 52 | 59.19 | 47.62 |

TABLE 5-continued

Primer Sequences for siRNA expression from *S. typhimurium* mutants

| HER2 | Sequence (5'→3') | Length | Start | Stop | Tm | GC % |
|---|---|---|---|---|---|---|
| Forward primer | GGTGGTCCTAGGGAGCTGTT (SEQ ID NO: 30) | 20 | 1 | 20 | 60.91 | 60.00 |
| Reverse primer | ATTTCTTTGTTCACAATTCCACACA (SEQ ID NO: 31) | 25 | 70 | 46 | 58.36 | 32.00 |

| NEG | Sequence (5'→3') | Length | Start | Stop | Tm | GC % |
|---|---|---|---|---|---|---|
| Forward primer | GGTGGTCCTAGGGAGCTGTT (SEQ ID NO: 32) | 20 | 1 | 20 | 60.91 | 60.00 |
| Reverse primer | CCCAATTGAAAAACGGCGCAT (SEQ ID NO: 33) | 21 | 119 | 99 | 60.94 | 47.62 |

REFERENCES

1. Hoffman, R M (2011) Tumor-seeking *Salmonella* amino acid auxotrophs. Current Opinion in Biotechnology 22:917-923.
2. Hoiseth S K and Stocker B A. (1981) Aromatic-dependent *Salmonella typhimurium* are non-virulent and effective as live vaccines. Nature 291:238-9.
3. Morrissey D, O'Sullivan G C and Tangney M (2010) Tumour Targeting with Systemically Administered Bacteria. Current Gene Therapy, 10, 3-14.

---

The invention claimed is:

1. A genetically transformed or transfected *Salmonella* SL7207 cell able to invade human tissue, wherein a chromosome of the genetically transformed or transfected *Salmonella* SL7207 cell expresses siRNA active against at least one gene encoding an oncogene, a chemo-resistant gene or a metabolic gene,
wherein said *Salmonella* SL7207 cell is transformed or transfected such that nucleic acid encoding said siRNA is stably integrated into the *Salmonella* SL7207 cell chromosome, and
wherein said siRNA is under the control of a pTAC promoter to enable expression of said siRNA within a tumour cell.

2. The genetically transformed or transfected *Salmonella* SL7207 cell of claim 1, wherein said oncogene gives rise to a solid tumour.

3. The genetically transformed or transfected *Salmonella* SL7207 cell of claim 1, wherein said oncogene is selected from the group consisting of: AR; C-MYC; BCL-2; and HER-2.

4. The genetically transformed or transfected *Salmonella* SL7207 cell of claim 1, wherein said chemo-resistant gene is Mdr1.

5. The genetically transformed or transfected *Salmonella* SL7207 cell of claim 1, wherein said metabolic gene is poly ADP ribose polymerase (PARP) or pro-angiogenic growth factor genes.

6. The genetically transformed or transfected *Salmonella* SL7207 cell according to claim 1, wherein said *Salmonella* SL7207 cell is modified using lambda red recombination or RecA-mediated recombination.

7. The genetically transformed or transfected *Salmonella* SL7207 cell according to claim 1, wherein said *Salmonella* SL7207 cell is modified at a location within the bacterial chromosome so that the nucleic acid encoding said siRNA is stably inherited at cell division in the absence of any selection.

8. The genetically transformed or transfected *Salmonella* SL7207 cell according to claim 1, wherein said siRNA comprises a strand of RNA that shares 50% or at least 75%, or at least 80%, 85%, 90%, 91%, 92%, 93%, 94%, 95%, 96%, 97%, 98% or 99%, complementarity to said oncogene, chemo-resistant gene or metabolic gene.

9. The genetically transformed or transfected *Salmonella* SL7207 cell according to claim 1, wherein said siRNA is complementary to the part of the oncogene, chemo-resistant gene or metabolic gene that comprises one or more genetic mutations that is/are responsible for the oncogenic nature of the oncogene or the or chemo-resistant nature of the chemo-resistant gene or the effect of the metabolic gene.

10. The genetically transformed or transfected *Salmonella* SL7207 cell of claim 1, wherein said *Salmonella* SL7207 cell is also genetically engineered such that it does not produce functional RNA degrading protein.

11. The genetically transformed or transfected *Salmonella* SL7207 cell of claim 1, wherein said siRNA is integrated in the mc gene.

12. The genetically transformed or transfected *Salmonella* SL7207 cell of claim 1, wherein said siRNA is selected from the group consisting of:

```
AAGAAGGCCAGTTGTATGGAC;        (SEQ ID NO: 1)

GAGCAAGAAGATGAGGAAG;          (SEQ ID NO: 2)

AACATCGCCCTGTGGATGACT;        (SEQ ID NO: 3)

AACAAAGAAATCTTAGACGAA;        (SEQ ID NO: 4)

CGGCGCATAAGAAGCATAT;          (SEQ ID NO: 5)

GTCCATACAACTGGCCTTCTT;        (SEQ ID NO: 6)

CTTCCTCATCTTCTTGCTC;          (SEQ ID NO: 7)

AGTCATCCACAGGGCGATGTT;        (SEQ ID NO: 8)

TTCGTCTAAGATTTCTTTGTT         (SEQ ID NO: 9)
and

ATATGCTTCTTATGCGCCG.          (SEQ ID NO: 10)
```

13. A method of treating cancer in a subject, comprising: administering an effective amount of the *Salmonella* SL7207 cell of claim 1 to a subject having or suspected of having cancer thereby arresting growth or reducing size of a tumour and treating the cancer in the subject.

\* \* \* \* \*

SEQUENCE LISTING

<160> NUMBER OF SEQ ID NOS: 33

<210> SEQ ID NO 1
<211> LENGTH: 21
<212> TYPE: DNA
<213> ORGANISM: Homo sapiens

<400> SEQUENCE: 1
aagaaggcca gttgtatgga c                                        21

<210> SEQ ID NO 2
<211> LENGTH: 19
<212> TYPE: DNA
<213> ORGANISM: Homo sapiens

<400> SEQUENCE: 2
gagcaagaag atgaggaag                                           19

<210> SEQ ID NO 3
<211> LENGTH: 21
<212> TYPE: DNA
<213> ORGANISM: Homo sapiens

<400> SEQUENCE: 3
aacatcgccc tgtggatgac t                                        21

<210> SEQ ID NO 4
<211> LENGTH: 21
<212> TYPE: DNA
<213> ORGANISM: Homo sapiens

<400> SEQUENCE: 4
aacaaagaaa tcttagacga a                                        21

-continued

```
<210> SEQ ID NO 5
<211> LENGTH: 19
<212> TYPE: DNA
<213> ORGANISM: Homo sapiens

<400> SEQUENCE: 5
cggcgcataa gaagcatat                                                      19

<210> SEQ ID NO 6
<211> LENGTH: 21
<212> TYPE: DNA
<213> ORGANISM: Homo sapiens

<400> SEQUENCE: 6
gtccatacaa ctggccttct t                                                   21

<210> SEQ ID NO 7
<211> LENGTH: 19
<212> TYPE: DNA
<213> ORGANISM: Homo sapiens

<400> SEQUENCE: 7
cttcctcatc ttcttgctc                                                      19

<210> SEQ ID NO 8
<211> LENGTH: 21
<212> TYPE: DNA
<213> ORGANISM: Homo sapiens

<400> SEQUENCE: 8
agtcatccac agggcgatgt t                                                   21

<210> SEQ ID NO 9
<211> LENGTH: 21
<212> TYPE: DNA
<213> ORGANISM: Homo sapiens

<400> SEQUENCE: 9
ttcgtctaag atttctttgt t                                                   21

<210> SEQ ID NO 10
<211> LENGTH: 19
<212> TYPE: DNA
<213> ORGANISM: Homo sapiens

<400> SEQUENCE: 10
atatgcttct tatgcgccg                                                      19

<210> SEQ ID NO 11
<211> LENGTH: 125
<212> TYPE: DNA
<213> ORGANISM: Artificial Sequence
<220> FEATURE:
<223> OTHER INFORMATION: siRNA vector

<400> SEQUENCE: 11
ggtggtccta gggagctgtt gacaattaat catcggctcg tataatgtgt ggaattgtga         60
agaaggccag ttgtatggac ttcaagagaa tatgcttctt atgcgccgtt tttcaattgg        120
gtggt                                                                    125

<210> SEQ ID NO 12
<211> LENGTH: 123
```

```
<212> TYPE: DNA
<213> ORGANISM: Artificial Sequence
<220> FEATURE:
<223> OTHER INFORMATION: siRNA vector

<400> SEQUENCE: 12
ggtggtccta gggagctgtt gacaattaat catcggctcg tataatgtgt ggaattgtga      60
agagcaagaa gatgaggatt caagagactt cctcatcttc ttgctctttt tcaattgggt     120
ggt                                                                   123

<210> SEQ ID NO 13
<211> LENGTH: 127
<212> TYPE: DNA
<213> ORGANISM: Artificial Sequence
<220> FEATURE:
<223> OTHER INFORMATION: siRNA vector

<400> SEQUENCE: 13
ggtggtccta gggagctgtt gacaattaat catcggctcg tataatgtgt ggaattgtga      60
acatcgccct gtggatgact tcaagagaa gtcatccaca gggcgatgtt tttttcaatt     120
gggtggt                                                               127

<210> SEQ ID NO 14
<211> LENGTH: 127
<212> TYPE: DNA
<213> ORGANISM: Artificial Sequence
<220> FEATURE:
<223> OTHER INFORMATION: siRNA vector

<400> SEQUENCE: 14
ggtggtccta gggagctgtt gacaattaat catcggctcg tataatgtgt ggaattgtga      60
acaaagaaat cttagacgaa ttcaagagat tcgtctaaga tttctttgtt tttttcaatt     120
gggtggt                                                               127

<210> SEQ ID NO 15
<211> LENGTH: 123
<212> TYPE: DNA
<213> ORGANISM: Artificial Sequence
<220> FEATURE:
<223> OTHER INFORMATION: siRNA vector

<400> SEQUENCE: 15
ggtggtccta gggagctgtt gacaattaat catcggctcg tataatgtgt ggaattgtgc      60
ggcgcataag aagcatattt caagagaata tgcttcttat gcgccgtttt tcaattgggt     120
ggt                                                                   123

<210> SEQ ID NO 16
<211> LENGTH: 20
<212> TYPE: DNA
<213> ORGANISM: Artificial Sequence
<220> FEATURE:
<223> OTHER INFORMATION: shRNA forward primer

<400> SEQUENCE: 16
ggtggtccta gggagctgtt                                                  20

<210> SEQ ID NO 17
<211> LENGTH: 21
<212> TYPE: DNA
<213> ORGANISM: Artificial Sequence
<220> FEATURE:
```

<223> OTHER INFORMATION: shRNA Reverse Primer

<400> SEQUENCE: 17
cccaattgaa aacggcgca t                                              21

<210> SEQ ID NO 18
<211> LENGTH: 19
<212> TYPE: DNA
<213> ORGANISM: Artificial Sequence
<220> FEATURE:
<223> OTHER INFORMATION: cMYC Forward Primer

<400> SEQUENCE: 18
gagcaagaag atgaggaag                                                19

<210> SEQ ID NO 19
<211> LENGTH: 19
<212> TYPE: DNA
<213> ORGANISM: Artificial Sequence
<220> FEATURE:
<223> OTHER INFORMATION: CMyc Reverse Primer

<400> SEQUENCE: 19
cttcctcatc ttcttgctc                                                19

<210> SEQ ID NO 20
<211> LENGTH: 22
<212> TYPE: DNA
<213> ORGANISM: Artificial Sequence
<220> FEATURE:
<223> OTHER INFORMATION: RNAse III gene forward primer

<400> SEQUENCE: 20
gacgatggca ataaatccgc ag                                            22

<210> SEQ ID NO 21
<211> LENGTH: 20
<212> TYPE: DNA
<213> ORGANISM: Artificial Sequence
<220> FEATURE:
<223> OTHER INFORMATION: RNAse III gene reverse primer

<400> SEQUENCE: 21
tcgtgtgctg gattgttgac                                               20

<210> SEQ ID NO 22
<211> LENGTH: 29
<212> TYPE: DNA
<213> ORGANISM: Artificial Sequence
<220> FEATURE:
<223> OTHER INFORMATION: Kanamycin Forward primer

<400> SEQUENCE: 22
ggtggtccta gggtggtcaa ttgcggttt                                     29

<210> SEQ ID NO 23
<211> LENGTH: 20
<212> TYPE: DNA
<213> ORGANISM: Artificial Sequence
<220> FEATURE:
<223> OTHER INFORMATION: kanamycin reverse primer

<400> SEQUENCE: 23
gaatactcat actcttcctt                                               20

```
<210> SEQ ID NO 24
<211> LENGTH: 19
<212> TYPE: DNA
<213> ORGANISM: Artificial Sequence
<220> FEATURE:
<223> OTHER INFORMATION: Forward Primer mutant siRNA expression

<400> SEQUENCE: 24
ggtggtccta gggagctgt                                               19

<210> SEQ ID NO 25
<211> LENGTH: 23
<212> TYPE: DNA
<213> ORGANISM: Artificial Sequence
<220> FEATURE:
<223> OTHER INFORMATION: reverse primer siRNA expresison

<400> SEQUENCE: 25
acaactggcc ttcttcacaa ttc                                          23

<210> SEQ ID NO 26
<211> LENGTH: 20
<212> TYPE: DNA
<213> ORGANISM: Artificial Sequence
<220> FEATURE:
<223> OTHER INFORMATION: Cmyc forward primer siRNA mutant expression

<400> SEQUENCE: 26
ggtcctaggg agctgttgac                                              20

<210> SEQ ID NO 27
<211> LENGTH: 21
<212> TYPE: DNA
<213> ORGANISM: Artificial Sequence
<220> FEATURE:
<223> OTHER INFORMATION: cMYc reverse primer siRNA mutant expression

<400> SEQUENCE: 27
ccacccaatt gaaaaagagc a                                            21

<210> SEQ ID NO 28
<211> LENGTH: 19
<212> TYPE: DNA
<213> ORGANISM: Artificial Sequence
<220> FEATURE:
<223> OTHER INFORMATION: BCL2 forward primer siRNA mutant expression

<400> SEQUENCE: 28
ggtggtccta gggagctgt                                               19

<210> SEQ ID NO 29
<211> LENGTH: 21
<212> TYPE: DNA
<213> ORGANISM: Artificial Sequence
<220> FEATURE:
<223> OTHER INFORMATION: BCl2 reverse primer siRNA mutant expression

<400> SEQUENCE: 29
acagggcgat gttcacaatt c                                            21

<210> SEQ ID NO 30
<211> LENGTH: 20
<212> TYPE: DNA
<213> ORGANISM: Artificial Sequence
<220> FEATURE:
<223> OTHER INFORMATION: HER2 forward primer siRNA mutant expression
```

```
<400> SEQUENCE: 30
ggtggtccta gggagctgtt                                                       20

<210> SEQ ID NO 31
<211> LENGTH: 25
<212> TYPE: DNA
<213> ORGANISM: Artificial Sequence
<220> FEATURE:
<223> OTHER INFORMATION: HER2 reverse primer siRNA mutant expression

<400> SEQUENCE: 31
atttctttgt tcacaattcc acaca                                                 25

<210> SEQ ID NO 32
<211> LENGTH: 20
<212> TYPE: DNA
<213> ORGANISM: Artificial Sequence
<220> FEATURE:
<223> OTHER INFORMATION: NEG forward primer siRNA mutant expression

<400> SEQUENCE: 32
ggtggtccta gggagctgtt                                                       20

<210> SEQ ID NO 33
<211> LENGTH: 21
<212> TYPE: DNA
<213> ORGANISM: Artificial Sequence
<220> FEATURE:
<223> OTHER INFORMATION: NEG Reverse primer siRNA mutant expression

<400> SEQUENCE: 33
cccaattgaa aaacggcgca t                                                     21
```